(12) United States Patent
Björling et al.

(10) Patent No.: US 6,961,613 B2
(45) Date of Patent: Nov. 1, 2005

(54) IMPLANTABLE BI-VENTRICULAR STIMULATION DEVICE AND SYSTEM, AND BI-VENTRICULAR STIMULATION AND SENSING METHOD

(75) Inventors: Anders Björling, Järfälla (SE); Nils Holmström, Järfälla (SE); Sven-Erik Hedberg, Kungsängen (SE); Asa Uhrenius, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 11 days.

(21) Appl. No.: 10/712,437

(22) Filed: Nov. 13, 2003

(65) Prior Publication Data

US 2004/0116971 A1 Jun. 17, 2004

(30) Foreign Application Priority Data

Dec. 16, 2002 (SE) .............................................. 0203728

(51) Int. Cl.[7] .............................................. A61N 1/365
(52) U.S. Cl. .......................................................... 607/9
(58) Field of Search ............................... 607/9, 14, 18, 607/27, 28

(56) References Cited

U.S. PATENT DOCUMENTS

| 5,720,768 | A | 2/1998 | Verboven-Nelissen |
| 6,070,100 | A | 5/2000 | Bakels et al. |
| 6,148,234 | A | 11/2000 | Struble |
| 6,473,645 | B1 * | 10/2002 | Levine ........................ 607/9 |
| 6,687,545 | B1 * | 2/2004 | Lu .............................. 607/28 |
| 2001/0049542 | A1 | 12/2001 | Florio et al. |
| 2002/0183795 | A1 | 12/2002 | Rouw et al. |

FOREIGN PATENT DOCUMENTS

| EP | 0 598 616 | 5/1994 |
| EP | 0 990 451 | 4/2000 |

* cited by examiner

*Primary Examiner*—George Manuel
(74) *Attorney, Agent, or Firm*—Schiff Hardin LLP

(57) ABSTRACT

An implantable bi-ventricular heart stimulating device has a control circuit that within a time cycle, delivers pacing pulses with both first and second pacing circuits with a time gap between a pacing pulse delivered by these pacing circuits. The time gap can be such that a pacing pulse delivered by the second pacing circuits falls substantially within a first time interval in which an evoked response can be expected to a pacing pulse delivered by the first pacing circuit. The control circuit performs a temporary modification of the operation of the device such that during at least one time cycle no pacing pulse is delivered by the second pacing circuit during the first time interval.

20 Claims, 3 Drawing Sheets

IMPLANTABLE BI-VENTRICULAR STIMULATION DEVICE AND SYSTEM, AND BI-VENTRICULAR STIMULATION AND SENSING METHOD

BACKGROUND OF THE INVENTION

1. Field of the Invention

The present invention relates to an implantable heart stimulating device with which it is possible to stimulate both the ventricles of a heart, i.e. a bi-ventricular pacer.

The invention also relates to a system including such a device and to a method for his bi-ventricular stimulation and sensing.

2. Description of the Prior Art

Many different implantable devices for stimulating a heart are known. The devices are normally able to sense the electrical activity of the heart. Some implantable devices are able to deliver stimulation pulses to both the left and right ventricles of the heart, and sometimes also to the left and right atria.

Devices that are able to deliver stimulation pulses to both the left and right ventricles are also called bi-ventricular pacers. Such devices can be used to treat patients who suffer from different severe cardiac problems, e.g. patients suffering from congestive heart failure (CHF). CHF is defined generally as the inability of the heart to deliver a sufficient amount of blood to the body. CHF can have different causes. It can for example be caused by a left bundle branch block (LBBB) or a right bundle branch block (RBBB). By using bi-ventricular pacing, for example, the contraction of the ventricles can be controlled in order to improve the ability of the heart to pump blood. The stimulation pulses to the two ventricles can be delivered simultaneously but it is also known for the stimulation pulses to the two ventricles to be delivered with a short time delay between them in order to optimise the pumping performance of the heart.

U.S. Pat. No. 5,720,768 describes different possible electrode positions in order to stimulate or sense the different chambers of the heart.

U.S. Pat. No. 6,070,100 describes that electrodes may be positioned in both the left and the right atrium as well as in the left and the right ventricles.

In connection with implantable pacers, in particular pacers which only have the possibility to stimulate the right ventricle, and sometimes also the right atrium, it is known to detect capture, i.e. to detect whether the heart actually reacts to a delivered stimulation pulse. If capture is not detected it is possible to cause the pacer to deliver a back-up pulse with a higher pulse energy than the first pulse. It is also possible to increase the pulse energy in future stimulation pulses if capture is not detected. In order to conserve the battery it is important for stimulation pulses not to be delivered with an unnecessarily high energy. By varying the energy of the stimulation pulses and by detecting the capture it is possible to find a threshold value for the stimulation pulse energy. Based on the threshold value, a suitable stimulation pulse energy can be determined.

The detection of capture involves several problems. Different signals from the heart or generated by the pacemaker may interfere with each other, which may make the detection of capture difficult. The evoked response that it is intended to detect may thus be hidden because of other electrical phenomena. It is particularly difficult to detect capture in a bi-ventricular pacer since in such a pacer there are more delivered and detected signals which may interfere with each other.

U.S. Pat. No. 6,148,234 describes a system for detecting capture in connection with bi-ventricular or bi-atrial pacing. The document describes the fact that if a chamber is captured, then there is a biological refractory period during which this chamber cannot be stimulated again. The system described in this document monitors these refractory periods for the different chambers, for example for the two ventricles. When capture is achieved in both ventricles, no intrinsic depolarization signals can be sensed during the following refractory period. However, where the output level of one of the pacing pulses is insufficient to capture one ventricle, but capture is achieved in the other ventricle, a delayed depolarization pattern can be detected in the ventricle that was not captured. This delayed depolarisation is due to an interventricular conduction from the ventricle that is captured to the ventricle that is not captured. The system according to this document thus monitors the refractory interval following each delivery of stimulating pulses to the ventricles. A loss of capture is indicated in case such a delayed depolarisation is sensed during the refractory period.

Also United States Patent Application Publication 2001/0049542 describes a system for detecting capture in connection with bi-ventricular or bi-atrial stimulation. The system includes a morphology detector incorporated in a micro controller to allow for the processing of the sensed intra-cardiac electrogram signals (IEGM). The morphology of the IEGM may depend on whether both the ventricles (or atria) have captured or not. By detecting the shape of the IEGM capture thus may be detected.

SUMMARY OF THE INVENTION

The present invention relates in particular to an implantable heart having a first pacing circuit adapted to be connected to a first pacing electrode suited to be positioned in or at a first ventricle of a heart so as to receive signals from said first pacing means such that the first pacing circuit is able to pace the first ventricle, a first sensing circuit adapted to be connected to a first sensing electrode suited to be positioned in or at the first ventricle of the heart so as to transfer signals to the first sensing circuit such that the first sensing circuit is able to sense the first ventricle, a second pacing circuit adapted to be connected to a second pacing electrode suited to be positioned in or at a second ventricle of the heart so as to receive signals from the second pacing circuit such that the second pacing circuit is able to pace the second ventricle, a second sensing circuit adapted to be connected to a second sensing electrode suited to be positioned in or at the second ventricle of the heart so as to transfer signals to the second sensing circuit such that the second sensing circuit is able to sense the second ventricle, a control circuit being able to detect an evoked response to a pacing pulse delivered by the first pacing circuit by sensing, with the first sensing circuit, within a first time interval that follows after a pacing pulse delivered by the first pacing circuit; the control circuit also being able to detect an evoked response to a pacing pulse delivered by said second pacing circuit by sensing, with the second sensing circuit, within a second time interval that follows after a pacing pulse delivered by the second pacing circuit, said control circuit being operable with time cycles corresponding to normal heart cycles and within one such time cycle, delivering pacing pulses with both the first pacing circuit and the second pacing circuit with a time gap between a pacing pulse delivered by the first pacing circuit and a pacing pulse delivered by the second pacing circuit, the control circuit operating with a time gap which is such that a pacing pulse delivered by the second pacing circuit falls substantially within the first time interval.

In such a device, the detection of an evoked response to a pacing pulse delivered by the first pacing circuit is difficult, since a pacing pulse is delivered by the second pacing circuit during the time interval in which an evoked response is to be sensed by the first sensing means.

An object of the invention is to provide an implantable heart stimulating device which overcomes the problem described in the previous paragraph. A further object is to provide such a device which is relatively uncomplicated and which can be implemented by relatively simple means.

The above objects are achieved in accordance with the invention by an implantable heart monitoring device of the type described above, in which the control circuit performs a temporary modification of the operation of the device such that during at least one time cycle no pacing pulse is delivered by the second pacing circuit during said first time interval.

Since no pacing pulse is delivered by the second pacing circuit during the first time interval, no pacing pulse from the second pacing circuit will interfere with the sensing of an evoked response during the first time interval. Consequently, it is possible to detect whether an evoked response is sensed during the first time interval.

In a preferred embodiment of the device, the control circuit undertakes the temporary modification of the operation by not delivering any pacing pulse by the second pacing circuit during the time cycle.

In another embodiment, the time gap (V-V) is decreased such that the pacing pulse delivered by the second pacing circuit comes substantially at the same time as the pacing pulse delivered by the first pacing circuit. "Substantially at the same time" as used herein means that the pacing pulse delivered by the second pacing circuit at least comes before the first time interval. This embodiment has the advantage that the second ventricle may still be paced although capture in the first ventricle can be confirmed.

In a further alternative, the time gap (V-V) is instead increased such that the pacing pulse delivered by the second pacing circuit comes after said first time interval. This alternative may be advantageous if during the normal operation of the device the pacing pulse delivered by the second pacing circuit is located quite late in time within the first time interval. This embodiment means that the pacing pulse delivered by the second pacing circuit is delayed such that it comes after the first time interval. Therefore, also in this case capture in the first ventricle may be confirmed.

Preferably, the temporary modification of the operation is performed during a number of time cycles. These time cycles can either follow immediately after each other or with a gap of one or more time cycles between them. In order to increase the reliability of the capture-detection concerning the first ventricle, the temporary modification preferably is carried out a number of times.

In another embodiment, the control circuit, during the aforementioned number of time cycles, varies the energy of the pacing pulses delivered by the first pacing circuit and detects, with the first sensing circuit, possible evoked responses during the first time interval such that a suitable pulse energy for the pacing pulses delivered by the first pacing circuit is determined. In this embodiment, a so-called stimulation threshold search is carried out for the pacing pulses delivered by the first pacing circuit.

The control circuit can either automatically initiate the temporary modification of the operation of the device at predetermined occasions in time, or in response to signals of a type that could be an indication of no capture by said first ventricle. One possibility is to operate the device with a first time window, and to sense, during the first time window, with the first sensing circuit, signals typical for an R-wave transferred from the second ventricle (or from some other part of the heart, such as the A-V-node) to the first ventricle, wherein the detection of such a signal typical of an R-wave constitutes the indication of no capture. As described above, a delayed depolarization pattern can be an indication of the fact that the ventricle in question has not captured. A detection of a typical R-wave during the first time window is thus an indication of the fact that the first ventricle may not have captured. Therefore, it is advantageous to use such a detection for initiating the above described temporary modification of the operation of the device in order to confirm whether capture is obtained or not.

The first time window preferably ends at least before 400 ms after the delivery of said pacing pulse by the first pacing circuit and starts between 0 ms and 150 ms after the delivery of the pacing pulse by the first pacing means. The first time window thus falls within the period that corresponds to the normal biological refractory period of the first ventricle.

The first time interval preferably starts 0–30 ms after the delivery of a pacing pulse by the first pacing circuit and is between 25 ms and 100 ms long. Analogously, the second time interval preferably starts 0 ms–30 ms after the delivery of a pacing pulse by the second pacing circuit and is between 25 ms and 100 ms long. These time intervals are suitable for detecting a possible evoked response in the respective ventricle.

The invention also encompasses an implantable heart stimulating system having a device according to any of the above embodiments and a first lead and a second lead connected to the device, wherein the first pacing electrode is arranged on the first lead and the second pacing electrode is arranged on the second lead. Preferably, the first sensing electrode is the same electrode as the first pacing electrode and the second sensing electrode is the same electrode as the second pacing electrode. With such a system, the advantages described above are achieved.

The invention also concerns a pacing method wherein the system is implanted in a human or animal, wherein the first pacing electrode is positioned in or at a first ventricle of the heart of the human or animal and wherein the second pacing electrode is positioned in or at the second ventricle of the heart. The system is preferably used in a human or animal suffering from congestive heart failure. The subject in question can suffer from a bundle branch block.

DESCRIPTION OF PREFERRED EMBODIMENTS

Figure 1:
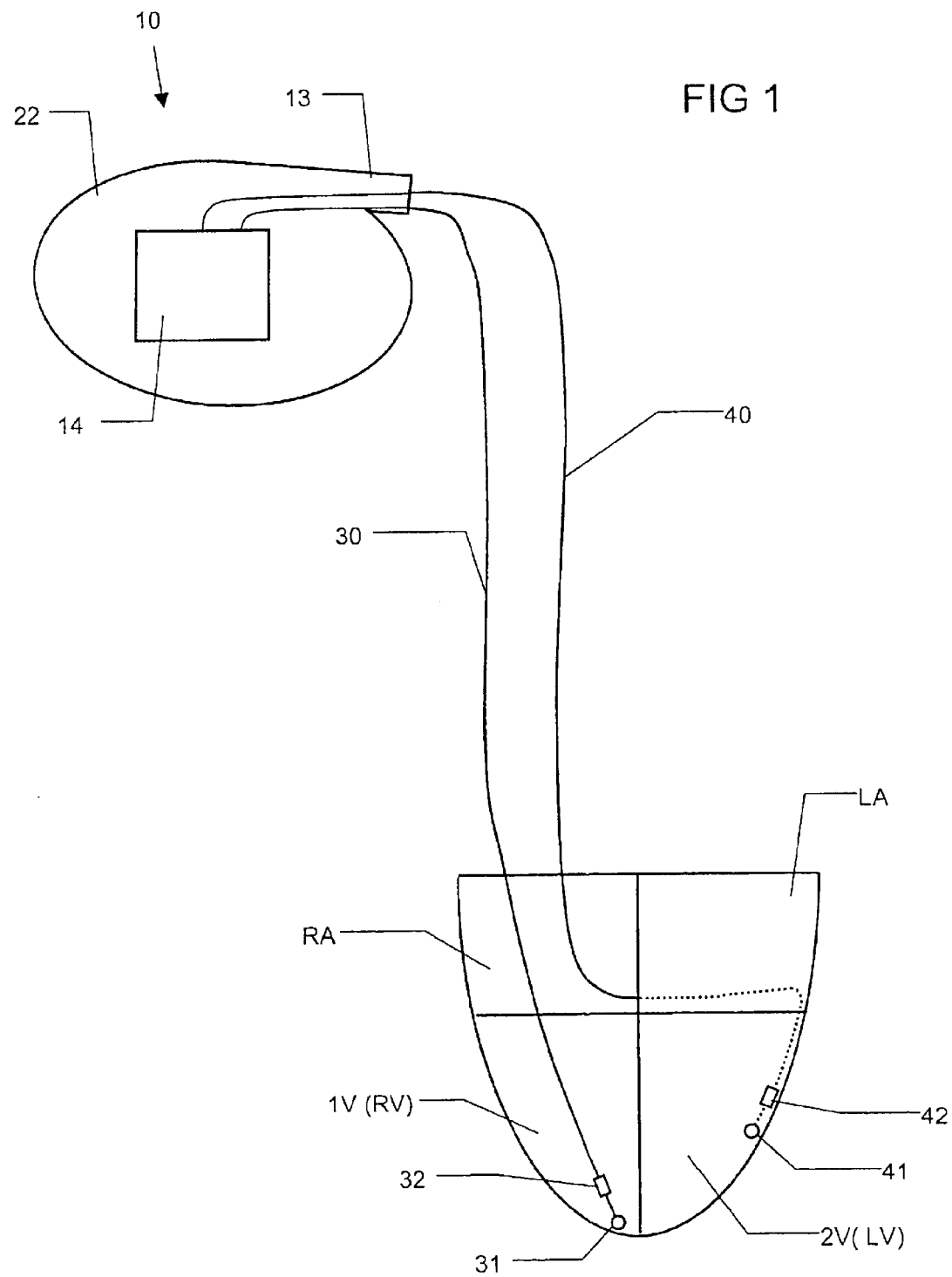
FIG. 1 schematically illustrates a heart stimulating system with a heart stimulating device connected to leads with sensing and pacing electrodes positioned in a heart.

FIG. 1 schematically shows an implantable heart stimulating device 10 according to the invention. The device 10 has a housing 22. The housing 22 contains a control circuit 14. The device 10 also has a connector portion 13. Via the connector portion 13, the device 10 can be connected to different leads. In FIG. 1 the device 10 is connected to a first lead 30 and to a second lead 40. The device 10 together with the first 30 and the second 40 leads constitute an implantable heart stimulating system according to the invention. The first lead 30 includes a pacing and sensing electrode 31, 32. In this example this electrode 31, 32 is a bipolar electrode with a tip portion 31 and a ring portion 32, however, it is within of the scope of the invention to instead use unipolar electrodes, as is known to those skilled in the art. The second lead 40 has a corresponding electrode 41, 42.

FIG. 1 also schematically illustrates a heart with a right atrium RA, a left atrium LA, a first ventricle 1V (which in this case is the right ventricle RV) and a second ventricle 2V (which in this case is the left ventricle LV). The electrode 31, 32 is positioned in the first ventricle 1V in order to be able to pace and sense this ventricle 1V. The electrode 41, 42 is positioned so as to pace and sense the second ventricle 2V. The second lead 40, for example, may be introduced via the right atrium RA and the coronary sinus such that the electrode 41, 42 is positioned in, for example, the middle or great cardiac vein of the heart. How to introduce the lead 40 in this manner is known to those skilled in the art. Although not shown in FIG. 1, it is also possible for the system to be connected to further leads with electrodes positioned in order to sense and/or pace the right atrium RA and the left atrium LA.

Figure 2:
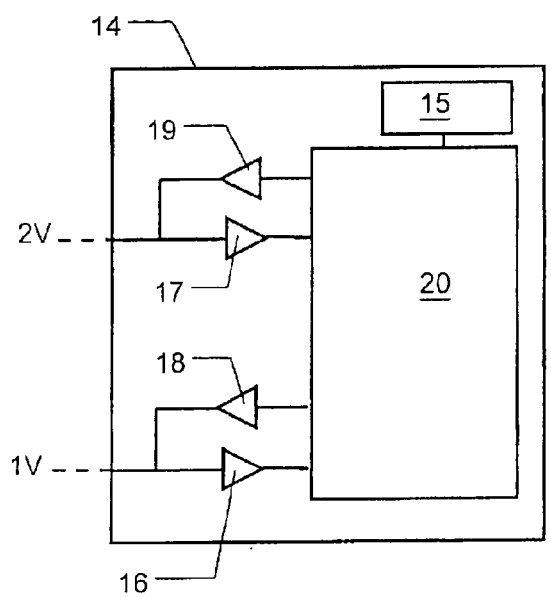
FIG. 2 schematically illustrates a control circuit in accordance with the invention for use in the device of FIG. 1.

FIG. 2 schematically shows the control circuit 14 in more detail. The control circuit 14 includes a memory 15 connected to a control portion 20. The control circuit 14 includes a first pacing circuit 18. The circuit 18 is adapted to be connected to a first pacing electrode 31, 32, which, as shown in FIG. 1, is positioned so as to receive signals from the first pacing circuit 18 such that the first pacing circuit 18 is able to pace the first ventricle 1V. The control circuit 14 also includes a first sensing circuit 16. The circuit 16 is adapted to be connected to a first sensing electrode 31, 32, which can be positioned in the first ventricle 1V in order to transfer signals to the first sensing circuit 16. In this manner the first sensing circuit 16 is able to sense the first ventricle 1V. Although the first pacing electrode could be a different electrode from the first sensing electrode, it is preferred that the same electrode 31, 32 is used both for pacing and sensing.

The control circuit 14 also includes a second pacing circuit 19 adapted to be connected to a second pacing electrode 41, 42 for pacing the second ventricle 2V of the heart. The control circuit 14 also includes a second sensing circuit 17 adapted to be connected to a second sensing electrode 41, 42 in order to be able to sense the second ventricle 2V of the heart. The second pacing electrode is preferably the same electrode as the second sensing electrode. The control circuit 14 of course also may include circuitry for pacing and sensing the atria of the heart.

Figure 4:
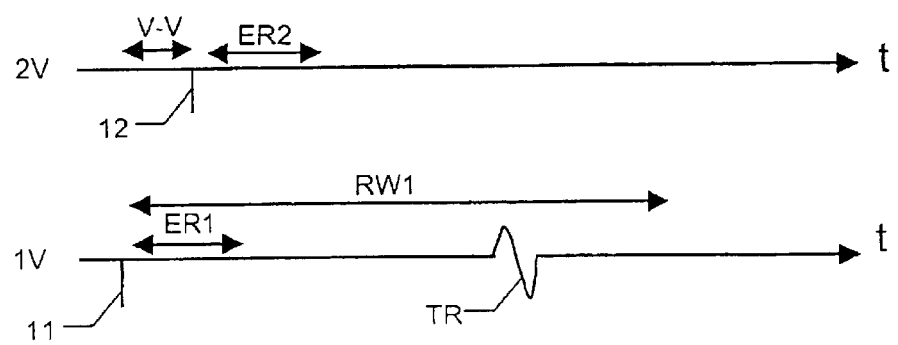
FIG. 4 schematically shows signals on a time scale related to first and second pacing and sensing circuits.

FIG. 4 schematically shows events related to the first ventricle 1V and the second ventricle 2V on a time scale. The marker 11 represents a pacing pulse delivered by the first pacing circuit 18 and the marker 12 represents a pacing pulse delivered by the second pacing circuit 19.

The control circuit 14 is able to detect an evoked response to a pacing pulse 11 delivered by the first pacing circuit 18 by sensing, with the first sensing circuit 16, within a first time interval ER1. The control circuit 14 also is able to detect an evoked response to the pacing pulse 12 delivered by the second pacing circuit 19 by sensing, with the second sensing circuit 17, within a second time interval ER2. Details of the control circuit 14 for detecting an evoked response are known to those skilled in the art. The first time interval ER1 may be set to begin, for example, 15 ms after the delivery of a pacing pulse 11 by the first pacing circuit 18. The length of the first time interval ER1 may be, for example, 50 ms. Analogously, the second time interval ER2 may start 15 ms after the delivery of a pacing pulse 12 by said second pacing circuit 19 and have a length of about 50 ms.

The control circuit 14 is operable with time cycles corresponding to normal heart cycles. Such an operation is normal for an implantable heart stimulating device. The time cycles are determined by preset timer intervals which also may depend on detected signals. The control circuit 14, within one such time cycle, delivers pacing pulses with both the first pacing circuit 18 and the second pacing circuit 19 with a time gap V-V between these pacing pulses.

It should be noted that, for a bi-ventricular pacer, it is known to be sometimes advantageous to deliver the pacing pulses with such a time gap V-V in order to optimize the blood-pumping ability of the heart. In the situation to which the present invention relates, the time gap V-V is such that a pacing pulse 12 is delivered by the second pacing circuit 19 at a point in time that falls within the mentioned first time interval ER1. It is thus difficult to detect an evoked response to a pacing pulse 11 delivered by the first pacing circuit 18. According to the invention, the control circuit 14 performs a temporary modification of the operation of the device 10 such that during at least one time cycle, no pacing pulse is delivered by the second pacing circuit 19 during the first time interval ER1.

The control circuit 14 can perform the temporary modification of the operation of the device 10 during a number of time cycles—either consecutive time cycles or intermittently. During the temporary modification of the operation, it is possible to detect an evoked response to a pacing pulse 11 delivered by the first pacing circuit 18, since no pacing pulse is delivered by the second pacing circuit 19 during the first time interval ER1. By modifying the operation of the device 10 over a number of time cycles, it is possible for the control circuit 14 to vary the energy of the pacing pulses 11 delivered by the first pacing circuit 18 and to detect, with the first sensing circuit 16, possible evoked responses during the first time interval ER1. By varying the pacing energy, a threshold value of the pulse energy can be determined. How to perform such a threshold search is known to those skilled in the art.

The control circuit 14 can automatically initiate the temporary modification of the device 10 at predetermined points in time, for example a predetermined number of times per day or per hour. Alternatively, it is also possible for the control circuit 14 to initiate the temporary modification of the operation upon the detection of signals which may be an indication of loss of capture in the first ventricle 1V.

With reference again to FIG. 4, it is difficult to detect an evoked response to the pacing pulse 11, since the pacing pulse 12 occurs within the first time interval ER1. However, if the first ventricle 1V is actually captured in response to the pacing pulse 11, then the first ventricle 1V will be in the biological refractory period during, for example, about 350 ms after the ventricle 1V was captured. During this biological refractory period, the first ventricle 1V cannot be depolarized again. However, if the first ventricle 1V is not captured but the second ventricle 2V is captured (as can be detected during the second time interval ER2), then, in accordance with the above description, the depolarization of the second ventricle 2V may reach the first ventricle 1V via the myocardium during the period that corresponds to the biological refractory period. It is also possible that such a transferred R-wave TR can originate from some other part of the heart, such as from the A-V-node. Such a transferred R-wave TR can be detected by the first sensing circuit 16. According to an embodiment of the present invention, the control circuit 14 therefore can be operated with a first time window RW1 so as to sense during this first time window RW1, with the first sensing circuit 16 signals that are typical for an R-wave TR transferred from the second ventricle 2V to the first ventricle 1V. The time that elapses before such a transferred R-wave TR is sensed by the first sensing circuit 16 depends on the particular case. The control circuit 14 can define a suitable duration for the first time window RW1. The first time window RW1, for example, may start directly after the delivery of the pacing pulse 11 by the first pacing circuit 19. The first time window RW1, y for example, may be 300 ms long. It should be noted that if the first time window RW1 coincides with the point in time when a pacing pulse 12, or a back-up pulse, is delivered by the second pacing circuits 19, then the sensing of a transferred R-wave TR preferably should be disabled for a short time around such a point or points in time. In other words: the time window RW1 should in this case include short blanking periods during which the sensing of a transferred R-wave is not possible.

Figure 3:
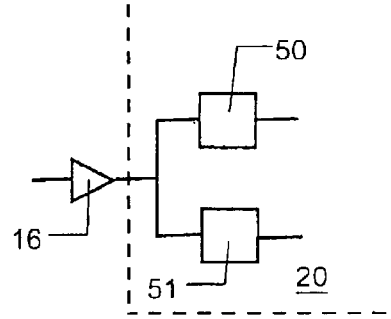
FIG. 3 is a somewhat more detailed illustration of part of the control circuit of FIG. 2.

It should be noted that the circuit arrangement for detecting an evoked response is preferably different from the arrangement for detecting other signals, such as a transferred R-wave TR. FIG. 3 schematically shows a part of the control circuit 14 in more detail. FIG. 3 illustrates that the first sensing circuit 16 is connected to an evoked response detection logic 50 and a P- or R-wave detection logic 51. The detection logics 50 and 51 can be seen to form part of the control portion 20 illustrated in FIG. 2. Similar detection logics may of course be arranged also for the second sensing circuit 17. The detection logic 50 thus is optimized to sense an evoked response and the detection logic 51 optimised to detect an R-wave. The detection logic 50 thus is active during the first time interval ER1 and the detection logic 51 is active during the first time window RW1. It is possible for the first time window RW1 to partly overlap with the first time interval ER1 if the detection logics 50, 51 are sufficiently different to distinguish the different signals from each other. According to an alternative embodiment, however, the first time window RW1 does not overlap with the first time interval ER1.

With reference again to FIG. 4, the control circuit 14 can be operate such that the detection of a transferred R-wave TR during the first time window RW1 will initiate the above described temporary modification of the operation of the device 10.

Figure 5A:
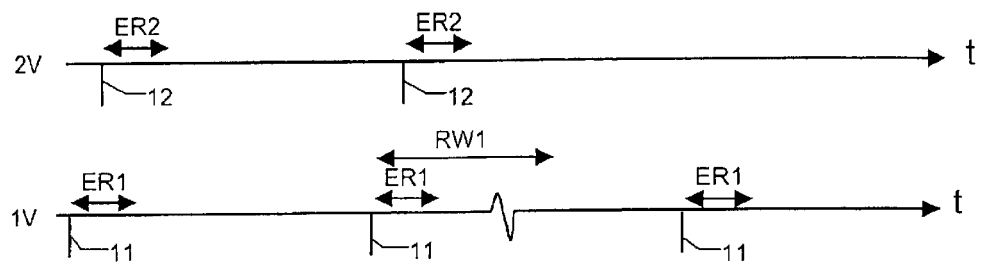
FIGS. 5a, 5b and 5c schematically illustrate the operation of the inventive device.
Figure 5B:
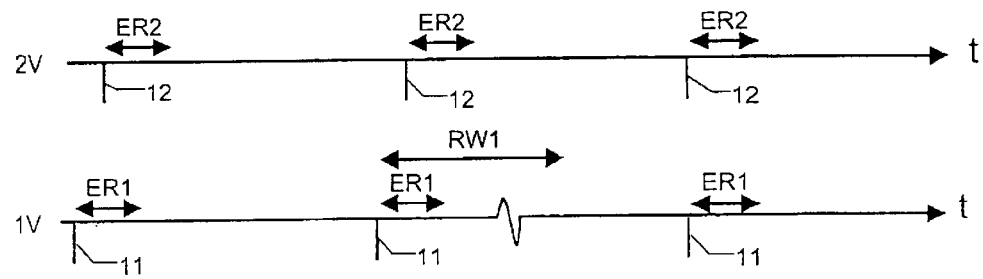
Figure 5C:
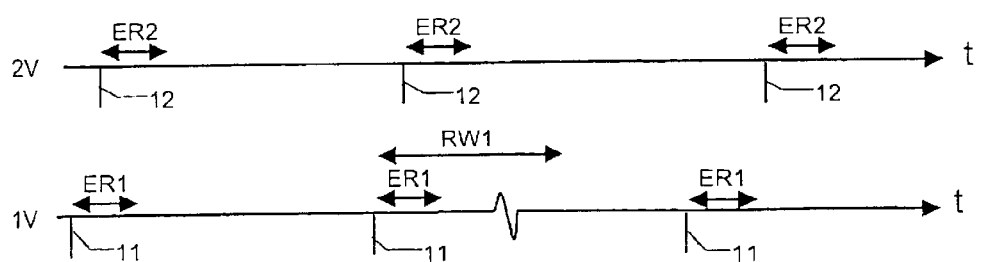

FIGS. 5a, 5b, and 5c illustrate three different manners of carrying out the temporary modification of the operation of the device 10. Each of the illustrations in FIGS. 5a, 5b and 5c show two time cycles where the operation of the device 10 is normal and a third time cycle where the temporary modification is performed. According to FIG. 5a, the control circuit 14 implements the temporary modification of the operation by not delivering any pacing pulse at all by the second pacing circuit 19 during the time cycle in question. According to FIG. 5b, the control circuit 14 implements the temporary modification by decreasing the time gap V-V such that the pacing pulses delivered by the first 18 and second 19 pacing circuits are at least substantially simultaneous. According to FIG. 5c, the control circuit implements the temporary modification is such that the time gap V-V is increased such that the pacing pulse 12 delivered by the second pacing circuits 19 comes after the first time interval ER1. In all these cases, it is thus possible to detect an evoked response also in the first ventricle 1V during the first time interval ER1.

The invention also concerns the use of an implantable heart stimulating system as illustrated in FIG. 1. The system is thereby implanted in a human or animal and the first pacing electrode 31, 32 is positioned in or at the first ventricle 1V and the second pacing electrode 41, 42 is positioned in or at the second ventricle 2V as described above. Preferably, the system is used on a human or animal suffering from congestive heart failure, for example caused by a bundle branch block.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable heart stimulating device comprising:

a first pacing circuit adapted for connection to a first pacing electrode, adapted for positioning for interaction with a first ventricle of a heart, to deliver signals from the first pacing circuit to pace the first ventricle;

a first sensing circuit adapted for connection to a first sensing electrode, adapted to be positioned for interaction with the first ventricle to supply signals to the first sensing circuit for sensing the first ventricle;

a second pacing circuit adapted for connection to a second pacing electrode, adapted to be positioned to interact with a second ventricle of the heart, to deliver signals from the second pacing circuit to the second ventricle to pace the second ventricle;

a second sensing circuit adapted for connection to a second sensing electrode, adapted to be positioned to interact with the second ventricle, to supply signals to the second sensing circuit to sense the second ventricle;

a control circuit operable with time cycles corresponding to normal cardiac cycles, said control circuit being connected to said first pacing circuit and to said first sensing circuit to detect an evoked response to a pacing pulse delivered by said first pacing circuit by sensing, via said first sensing circuit, within a first time interval following said pacing pulse delivered by said first pacing circuit;

said control circuit being connected to said second pacing circuit and said second sensing circuit for detecting an evoked response to a pacing pulse delivered by said second pacing circuit by sensing, via said second sensing circuit, within a second time interval following the pacing pulse delivered by said second pacing circuit;

said control circuit, within one of said time cycles, causing said first and second pacing circuits to respectively deliver pacing pulses with a time gap therebetween, said pacing pulse delivered by said second pacing circuit falling substantially within said first time interval and thereby masking detection of an evoked response to a pacing pulse delivered by the first pacing circuit; and said control circuit spontaneously temporarily modifying delivery of the pacing pulses by said second pacing circuit so that, during at least one of said time cycles, no pacing pulse is delivered by said second pacing circuit during said first time interval.

2. An implantable heart stimulating device as claimed in claim 1 wherein said control circuit temporarily modifies delivery of said pacing pulses by said second pacing circuit by causing said second pacing circuit to not deliver any pacing pulses during said at least one time cycle.

3. An implantable heart stimulating device as claimed in claim 1 wherein said control circuit temporarily modifies delivery of said pacing pulses by said second pacing circuit by, during said at least one time cycle, decreasing said time gap so that said second pacing circuit delivers a pacing pulse at substantially a same time as a pacing pulse delivered by said first pacing circuit.

4. An implantable heart stimulating device as claimed in claim 1 wherein said control circuit temporarily modifies delivery of said pacing pulses by said second pacing circuit by, during said at least one time cycle, increasing said time gap so that a pacing pulse delivered by said second pacing circuit occurs after said first time interval.

5. An implantable heart stimulating device as claimed in claim 1 wherein said control circuit temporarily modifies delivery of said pacing pulses by said second pacing circuit during a plurality of said time cycles.

6. An implantable heart stimulating device as claimed in claim 5 wherein said time cycles in said plurality of time cycles immediately follow each other in succession.

7. An implantable heart stimulating device as claimed in claim 5 wherein said time cycles in said plurality of said time cycles do not immediately follow each other and are respectively separated by at least one time cycle.

8. An implantable heart stimulating device as claimed in claim 5 wherein said control circuit, during said plurality of said time cycles, varies an energy of the pacing pulses delivered by said first pacing circuit and detects, via said first sensing circuit, occurrences of evoked responses during said first time interval to determine an appropriate energy for the pacing pulses delivered by said first pacing circuit.

9. An implantable heart stimulating device as claimed in claim 1 wherein said control circuit automatically initiates said temporary modification of the delivery of said pacing pulses by said second pacing circuit at predetermined points in time.

10. An implantable heart stimulating device as claimed in claim 1 wherein said control circuit initiates said temporary modification of the delivery of said pacing pulses by said second pacing circuit upon detection of at least one signal indicative of an absence of capture by said first ventricle.

11. An implantable heart stimulating device as claimed in claim 10 wherein said control circuit senses in a first time window, via said first sensing circuit, signals representatives of an R-wave in said first ventricle, transferred to said first ventricle from another region of the heart, and wherein said first time window does not coincide with said first time interval and does not start before a pacing pulse delivered by said first pacing circuit, and wherein said signal indicative of an R-wave is said signal indicative of an absence of capture.

12. An implantable heart stimulating device as claimed in claim 11 wherein said control circuit causes said first time window before 400 ms after delivery of said pacing pulse by said first pacing circuit.

13. An implantable heart stimulating device as claimed in claim 11 wherein said control circuit causes said first time window to start between 0 ms and 150 ms after the delivery of said pacing pulse by said second pacing circuit.

14. An implantable heart stimulating device as claimed in claim 1 wherein said control circuit starts said first time interval at a time in a range between 0 and 30 ms after the delivery of a pacing pulse by said first pacing circuit, and sets said first time interval to a duration between 25 and 100 ms.

15. An implantable heart stimulating device as claimed in claim 1 wherein said control circuit starts said second time interval at a time in a range between 0 and 30 ms after the delivery of a pacing pulse by said second pacing circuit, and sets said second time interval to a duration between 25 and 100 ms.

16. An implantable heart stimulating system comprising:

a first pacing electrode adapted for positioning for interaction with a first ventricle of a heart;

a first pacing circuit connected to said first pacing electrode to deliver signals from the first pacing circuit to pace the first ventricle;

a first sensing electrode adapted to be positioned for interaction with the first ventricle;

a first sensing circuit connected to said first sensing electrode to supply signals to the first sensing circuit for sensing the first ventricle;

a second pacing electrode adapted to be positioned to interact with a second ventricle of the heart;

a second pacing circuit connected to said second pacing electrode to deliver signals from the second pacing circuit to the second ventricle to pace the second ventricle;

a second sensing electrode adapted to be positioned to interact with the second ventricle;

a second sensing circuit connected to said second sensing electrode to supply signals to the second sensing circuit to sense the second ventricle;

a control circuit operable with time cycles corresponding to normal cardiac cycles, said control circuit being connected to said first pacing circuit and to said first sensing circuit to detect an evoked response to a pacing pulse delivered by said first pacing circuit by sensing, via said first sensing circuit, within a first time interval following said pacing pulse delivered by said first pacing circuit;

said control circuit being connected to said second pacing circuit and said second sensing circuit for detecting an evoked response to a pacing pulse delivered by said second pacing circuit by sensing, via said second sensing circuit, within a second time interval following the pacing pulse delivered by said second pacing circuit;

said control circuit, within one of said time cycles, causing said first and second pacing circuits to respectively deliver pacing pulses with a time gap therebetween, said pacing pulse delivered by said second pacing circuit falling substantially within said first time interval and thereby masking detection of an evoked response to a pacing pulse delivered by the first pacing circuit; and said control circuit spontaneously temporarily modifying delivery of the pacing pulses by said second pacing circuit so that, during at least one of said time cycles, no pacing pulse is delivered by said second pacing circuit during said first time interval.

17. An implantable heart stimulating system as claimed in claim 1 wherein said first sensing electrode and said first pacing electrode are a same electrode, and wherein said second sensing electrode and said second pacing electrode are a further, same electrode.

18. A method for bi-ventricular stimulation and sensing of a heart, comprising the steps of:

connecting a first pacing circuit adapted for connection to a first pacing electrode and positioning said first pacing electrode for interaction with a first ventricle of a heart, to deliver signals from the first pacing circuit to pace the first ventricle;

connecting a first sensing circuit to a first sensing electrode and positioning said first sensing electrode for interaction with the first ventricle to supply signals to the first sensing circuit for sensing the first ventricle;

connecting a second pacing circuit to a second pacing electrode and positioning said second pacing electrode to interact with a second ventricle of the heart, to deliver signals from the second pacing circuit to the second ventricle to pace the second ventricle;

connecting a second sensing circuit to a second sensing electrode and positioning said second sensing electrode to interact with the second ventricle, to supply signals to the second sensing circuit to sense the second ventricle;

operating a control circuit with time cycles corresponding to normal cardiac cycles and connecting said control circuit to said first pacing circuit and to said first sensing circuit for detecting an evoked response to a pacing pulse delivered by said first pacing circuit by sensing, via said first sensing circuit, within a first time interval following said pacing pulse delivered by said first pacing circuit;

connecting said control circuit to said second pacing circuit and said second sensing circuit for detecting an evoked response to a pacing pulse delivered by said second pacing circuit by sensing, via said second sensing circuit, within a second time interval following the pacing pulse delivered by said second pacing circuit;

via said control circuit, within one of said time cycles, causing said first and second pacing circuits to respectively deliver pacing pulses with a time gap therebetween, said pacing pulse delivered by said second pacing circuit following substantially within said first time interval and thereby masking detection of an evoked response to a pacing pulse delivered by the first pacing circuit; and via said control circuit, spontaneously temporarily modifying delivery of the pacing pulses by said second pacing circuit so that, during at least one of said time cycles, no pacing pulse is delivered by said second pacing circuit during said first time interval.

19. A method as claimed in claim 18 comprising selecting said pacing pulses to treat congestive heart failure of said heart.

20. A method as claimed in claim 18 comprising selecting said pacing pulses to treat a bundle branch block of the heart.

* * * * *